United States Patent
Ogawa et al.

(10) Patent No.: US 6,268,359 B1
(45) Date of Patent: Jul. 31, 2001

(54) PREVENTIVES OR REMEDIES FOR VISION DISORDERS

(75) Inventors: Takahiro Ogawa, Nishinomiya; Noriko Watanabe, Suita; Mitsunori Waki, Kobe, all of (JP)

(73) Assignees: Senju Pharmaceutical Co., Ltd., Osaka; Yamanouchi Pharmaceutical Co., Ltd., Tokyo, both of (JP)

( * ) Notice: Subject to any disclaimer, the term of this patent is extended or adjusted under 35 U.S.C. 154(b) by 0 days.

(21) Appl. No.: 09/601,216

(22) PCT Filed: Jan. 25, 1999

(86) PCT No.: PCT/JP99/00261

§ 371 Date: Jul. 28, 2000

§ 102(e) Date: Jul. 28, 2000

(87) PCT Pub. No.: WO99/38533

PCT Pub. Date: Aug. 5, 1999

(30) Foreign Application Priority Data

Jan. 28, 1998 (JP) .................................................. 10-015538

(51) Int. Cl.[7] ..................................................... A61K 31/55
(52) U.S. Cl. ........................... 514/215; 514/213; 514/220
(58) Field of Search ................................. 514/457, 578, 514/577, 215, 423, 220, 554, 256, 304, 316, 317

(56) References Cited

U.S. PATENT DOCUMENTS

| | | | |
|---|---|---|---|
| 4,853,375 | * 8/1989 | Krupin et al. | 514/152 |
| 5,055,448 | 10/1991 | Manning et al. | . |
| 5,204,349 | 4/1993 | Bock et al. | . |
| 5,258,510 | 11/1993 | Ogawa et al. | . |
| 5,300,513 | 4/1994 | Ogawa et al. | . |
| 5,512,563 | * 4/1996 | Albright et al. | 514/211 |
| 5,663,431 | 9/1997 | Di Malta et al. | . |

FOREIGN PATENT DOCUMENTS

| | | |
|---|---|---|
| 0346068 | 12/1989 | (EP) . |
| 044898 | 9/1991 | (EP) . |
| 0496452 | 7/1992 | (EP) . |
| 0532097 | 3/1993 | (EP) . |
| 0533243 | 3/1993 | (EP) . |
| 0620003 | 10/1994 | (EP) . |
| 0709386 | 5/1996 | (EP) . |
| 2-19397 | 1/1990 | (JP) . |
| 2-32098 | 2/1990 | (JP) . |
| 3-127732 | 5/1991 | (JP) . |
| 4-321669 | 11/1992 | (JP) . |
| 5-4984 | 1/1993 | (JP) . |
| 5-112600 | 5/1993 | (JP) . |
| 5-230027 | 9/1993 | (JP) . |
| 5-294961 | 11/1993 | (JP) . |
| 6-135992 | 5/1994 | (JP) . |
| 6-211800 | 8/1994 | (JP) . |
| 7-233073 | 9/1995 | (JP) . |
| 7-242625 | 9/1995 | (JP) . |
| 7-247269 | 9/1995 | (JP) . |
| 8-198879 | 8/1996 | (JP) . |
| 8-231403 | 9/1996 | (JP) . |
| 95/03301 | 2/1995 | (WO) . |
| 95/03305 | 2/1995 | (WO) . |

OTHER PUBLICATIONS

Kinter, Lewis B. et al., Discovery and Therapeutic Utility of Vasopressin Antagonists in Rats., Journal of Cardiovascular Pharmacology, 1986, vol. 8, Suppl. 7, S36–S43, Summary, S37 left column, lines 37 to 55.

Chem. abstr., vol. 90, 1979 (Columbus, OH, USA), the abstract No. 81328, Nagasubramanian, S., Role of pituitary vasopressin in the formation and dynamics of aqueous humor, Trans. Ophthalmol. Soc. U.K., 1977, 97(4), 686–701(Eng).

Nagasubramanian, S., Role of pituitary vasopressin in the formation and dynamics of aqueous humor, Trans. Ophthalmol. Soc. U.K., 1977, 97(4), 686–701.

Chemical Abstracts, vol. 82, 1975 (Columbus, OH, USA), the abstract No. 26356, Cole, D.F. et al., Action of vasopressins on intraocular pressure in rabbits, IRCS Libr. Compend., 1974, 1(1), 15.11.1.

Wallace, et al., Effects of Systemic Desmopressin on Aqueous Humor Dynamics in Rabbits, Investigative Ophthalmalogy & Visual Science, vol. 29, No. 3, Mar. 1988, pp. 406–410.

* cited by examiner

*Primary Examiner*—Zohreh Fay
*Assistant Examiner*—Brian-Yong Kwon
(74) *Attorney, Agent, or Firm*—Wenderoth, Lind & Ponack, L.L.P.

(57) ABSTRACT

A pharmaceutical composition for preventing or treating visual function disorders caused by ocular circulatory disorders (for example, ocular hypertension and glaucoma) and visual function disorders based on ciliary tension (for example, myopia) whose active component is a vasopressin antagonist.

8 Claims, 3 Drawing Sheets

Fig. 1

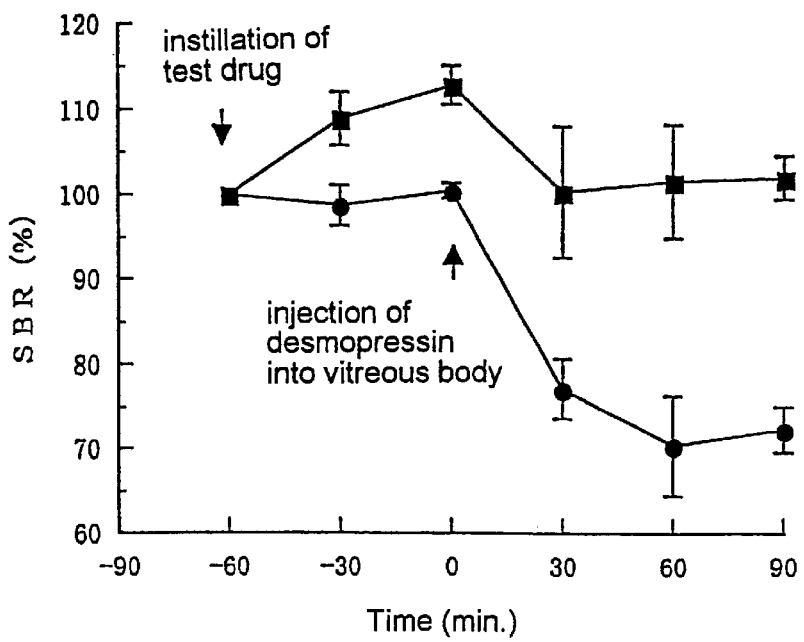

Effect of test drug on change in blood flow of optic disc (■) Test drug-   (●) Control eye
    instilled eye SBR: The rate of a change in blood flow per time at a laser speckle (a random speckled pattern formed at an image focal plane by interference of scattered light upon irradiation of a laser to a living tissue) and is represented the value obtained by squaring a blur rate calculated by dividing an average amount of light with a light variation at each pixel (standard deviation).

Change in intraocular pressure after injection of test drug in anterior chamber aqueous humor (■) test drug-injected eye (●) control eye

*: $p < 0.05$, **: $p < 0.01$

○ control
● test drug 1 × $10^{-7}$M
▲ test drug 1 × $10^{-8}$M

PREVENTIVES OR REMEDIES FOR VISION DISORDERS

This application is a 371 application of PCT/JP99/00261 filed Jan. 25, 1999.

FIELD OF THE INVENTION

The present invention relates to a pharmaceutical composition for preventing or treating visual function disorders caused by disorders of ocular circulation such as intraocular blood circulation and aqueous humor circulation, as well as ciliary muscle tension and the like.

BACKGROUND OF THE INVENTION

In intraocular blood circulation, ophthalmic artery enters into orbit and branches to central retinal artery, lacrimal artery, posterior ciliary artery and anterior ciliary artery. Then, the blood circulation flows out of the eye through retinal central vein, vortex vein and ophthalmic vein. Anterior ciliary artery connects to blood vessel systems of choroid, optic disk, iris, ciliary body and the like. Therefor, it is known that, when the blood vessel systems are damaged, diseases such as glaucoma (in particular, open angle glaucoma and normal pressure glaucoma), pigmentary retinal degeneration, macular degeneration, ischemic optic neuropathy, choroid diseases following iridocyclitis, and retinochoroiditis are induced, and visual functions are damaged.

As hitherto known factors which cause intraocular blood circulatory disorders, among physiological active substances produced in vascular endothelial cells, there are those contacting blood vessel smooth muscle cells such as endothelin, thromboxane A2, angiotensin II and endogenous amines (dopamine, epinephrine, serotonin and the like). However, ocular blood flow varies largely due to difference in species, individuals and ocular tissues. In addition, ocular circulation measurement is still developing. Then, factors which cause intraocular blood circulatory disorders have not yet been fully elucidated.

Currently, for chemotherapy of diseases accompanied with ocular blood circulatory disorders, tocopherol nicotinate which is vitamin E medicine, micro-circulatory improving medicine such as pentoxifyline, and various steroids are administrated orally. However, there are problems such as insufficient ocular circulatory improving activity, and side effects, for example, hypotension and gastrointestinal disorders. It is also known that diseases such as ocular hypertension and closed angle glaucoma are caused by aqueous humor circulatory disorders. In glaucoma, the ocular hypertension causes disorders of the axon of optic nerve, which results in visual function disorders such as disorders of optic disk and abnormal visual field. For treatment of glaucoma, there are instillation of cholinergic agents whose typical example is pilocarpin which contracts ciliary muscle to stimulate outflow of aqueous humor; instillation of sympathomimetic agents such as epinephrine and dipivefrine which inhibit production of aqueous humor; and instillation of sympathomimetic β-blockers such as timolol, pindolol and carteolol; as well as oral administration of carbonic anhydrase inhibitors such as acetazolamide; and instillation of prostaglandin derivatives which promote uveoscleral outflow of aqueous humor by relaxing of ciliary muscle to promote outflow of aqueous humor. However, these drugs have problems such as various side effects depending on their respective activities.

Further, recently, many persons have been required to continue working at a short visual range as a factor of the living environment. This has caused ciliary muscle tension, resulting in visual function disorders such as refractive errors, for example, tonic accommodative myopia and myopia. Although instillation of control paralytic agents such as atropine and tropicamide have been tried to inhibit progress of myopia, this treatment is not popularized in the clinical field because of unreliability of effects and side effects such as mydriasis.

OBJECTS OF THE INVENTION

An object of the present invention is to provide a pharmaceutical composition for preventing or treating visual function disorders caused by ocular circulatory disorders, ciliary muscle tension, and the like, which improves the above problems. The term "ocular circulation" used herein means "intraocular blood circulation" and "aqueous humor circulation".

SUMMARY OF THE INVENTION

The present inventors have studied intensively to develop a pharmaceutical composition for preventing or treating visual function disorders which have both excellent ocular circulation improving and ciliary muscle relaxing activities and are highly safe. As a result, it has been found that vasopressin antagonists exhibit the desired ocular circulation improving activity and ciliary muscle relaxing activity.

That is, vasopressin is known as a substance in a living body which contracts blood vessel smooth muscle, and its antagonists are proposed to be useful for prevention or treatment of diseases caused by blood circulatory disorders. However, it has not been reported heretofore in the prior art that vasopressin antagonists improve ocular circulation, exhibit intraocular pressure reducing activity and improve myopia. Further, no report of the application of vasopressin antagonists to the opthalomological field involving glaucoma has been found.

For example, JP 2-19397 A and JP 2-32098 A disclose the use of peptide derivatives, which are useful for vasopressin antagonists, as hypotensors and the like, and JP 3-127732 A discloses the use of indole derivatives, which are useful for vasopressin antagonists, as agents for preventing and treating hypertension, circulatory disfunction and the like. However, they do not disclose any application thereof in the ophthalmological field. JP 4-321669 A discloses that benzo-heterocyclic compounds are useful as vasopressin antagonists and can be used as vasodepressors, hypotensors, diuretics, platelet agglutination depressors and the like. JP 5-4984 A discloses the use of carbostyril derivatives, which are useful as vasopressin antagonists, as hypotensors. However, there is no disclosure of the use thereof in the ophthalmological field. JP 5-112600 A discloses cyclic hexapeptide oxytocin antagonists, and JP 5-294961 A and JP 5-230027 A disclose spiro-indanyl-camphorsulfonyl oxytocin antagonists. However, they disclose only the use thereof as repressors of premature delivery and the like. Although JP 6-135992 A discloses endothelin receptor antagonists from microorganisms which are also useful as vasopressin antagonists, they disclose only the use thereof in treatment of cardiovascular disorder and the like. JP 6-211800 A discloses benzo-heterocyclic compounds and their use for preventing and treating hypertension, premature delivery and the like. However, no use in the ophthalmological field is disclosed.

JP 7-233073 A discloses a vasopressin antagonist composition comprising as active component an amino acid, but it discloses only the use thereof in prevention and treatment of kidney function disorders, hepatocirrhosis and the like. JP 7-242625 A discloses piperidinyl-camphorsulfonyl oxytocin antagonist, but it discloses only the use thereof in prevention and treatment of hypertension, premature delivery and the like. JP 7-247269 A discloses indole derivatives useful for vasopressin antagonists, but it discloses only the use thereof in treatment of diseases in cardiovascular, kidney, stomach and the like.

WO95/03305 discloses nitrogen-containing aromatic 5-membered ring-condensed benzazepine derivatives, JP 8-198879 A discloses a novel method for producing the benzazepine derivatives, and JP 8-231403 A discloses a stable aqueous solution using one of the benzazepine derivatives. However, they do not suggest the use of vasopressin antagonists in the ophthalmological field, either.

Further, it is reported that, when desmopressin which is a vasopressin derivative is administrated intravenously, intraocular pressure is increased due to acceleration of aqueous humor production (Investigative Ophthalmology Visual Science, Vol. 29, 406–410, 1988). Then, there is a possibility that vasopressin may be one of factors that control intraocular pressure. However, there is no suggestion of improvement of ocular circulation, intraocular pressure reducing activity and improvement of myopia by vasopressin antagonist.

Under these circumstances, the present inventors have found that vasopressin antagonists exhibit excellent and highly safe preventing and treating activities for visual function disorders.

The present invention has been completed based on the above the present inventors' novel findings and provides a pharmaceutical composition for preventing and treating visual function disorders comprising as an active component a vasopressin antagonist.

BRIEF DESCRIPTION OF DRAWINGS

FIG. 1 illustrates the test results of Test Example 2, hereinafter.

DETAILED DESCRIPTION OF THE INVENTION

Figure 2:
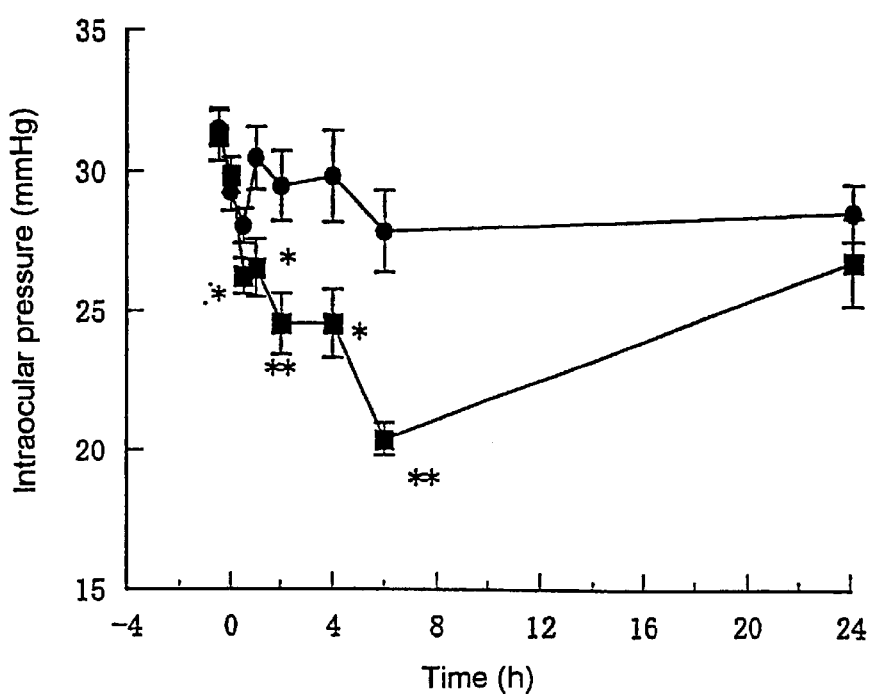
FIG. 2 illustrates the test results of Test Example 3, hereinafter.

The vasopressin antagonists used in the present invention are not specifically limited, but it is preferred to use the vasopressin antagonists disclosed in the above JP 2-19397 A, JP 2-32098 A, JP 03-127732 A, JP 4-321669 A, JP 5-4984 A, JP 5-112600 A, JP 5-294961 A, JP 5-230027 A, JP 6-135992 A, JP 6-211800 A, WO95/03305, JP 7-242625 A and JP 7-247269 A as well as JP 2-218653 A, JP 4-154765 A, WO96/41795 and the like, in particular benzazepine derivatives disclosed in the above WO95/03305 of the formula (I):

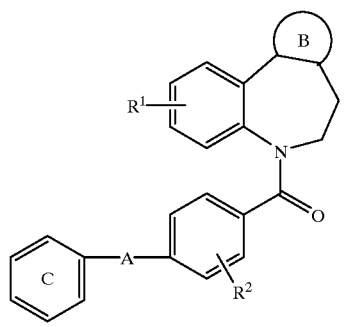

wherein:
ring B is a nitrogen-containing aromatic 5-membered ring having at least one nitrogen atom and optionally one oxygen or sulfur atom, which may have substituent(s);
$R^1$ and $R^2$ are the same or different, and each is a hydrogen atom, a halogen atom, a lower alkyl group, an amino group which may be substituted by lower alkyl group(s), or a lower alkoxy group;
A is a single bond or a group represented by the formula: —NHCO—$(CR^3R^4)_n$—;
n is 0 or an integer of 1 to 3;
$R^3$ and $R^4$ may be the same or different, and each is a hydrogen atom or a lower alkyl group, or $R^3$ together with $R^4$ may form a lower alkylene group having 2 to 7 carbon atoms; and
ring C is a benzene ring which may have substituent(s); or a pharmaceutically acceptable salt thereof.

The compound of the formula (I) which is a vasopressin antagonist suitable for using in the present invention is the known compound disclosed in WO95/03305, and can be prepared by the production process disclosed therein or JP 8-198879 A.

In the formula (I), unless otherwise stated, the term "lower alkyl group" means a straight- or branched alkyl group having 1 to 6 carbon atoms, "lower alkenyl group" and "lower alkynyl group" mean straight- or branched groups having 2 to 6 carbon atoms, and "cycloalkyl group" means group having 3 to 8 carbons.

In the compound of the formula (I), there may be optical isomers due to the asymmetric carbon atom, or geometrical isomers due to the double bond or the cyclohexane ring. These isomers including their isolated forms and mixtures thereof are represented by the formula (I). Also included are their hydrates, solvates, polymorphs and mixtures thereof.

In the compound of the formula (I), examples of ring B include formula:

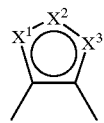

wherein;
one of $X^1$ and $X^3$ is a group represented by the formula =N—, and the other is a group represented by the formula —$NR^5$—, —O—, —S— or =N—;
$X^2$ is a group represented by the formula =$CR^6$—, —O—, —S— or =N—,
$R^5$ is a hydrogen atom or a lower alkyl group; and $R^6$ is
a) a hydrogen atom,
b) a lower alkyl group, a lower alkenyl group or a lower alkynyl group, each of which is unsubstituted or substituted,
c) a cycloalkyl group having 3 to 8 carbon atoms,
d) an amino group which may have substituent(s), a 1-pyrrolidinyl group, a piperidino group, a morpholino group, or a 1-piperazinyl, 1-imidazolidinyl or 1-homopiperazinyl group which may be substituted by a lower alkyl group at the ring nitrogen atom,
e) a guanidino group or an amidino group, or
f) a hydroxyl group, a lower alkoxyl group, a mercapto group, or a lower alkylthio group. Preferably, the ring B is represented by the formula:

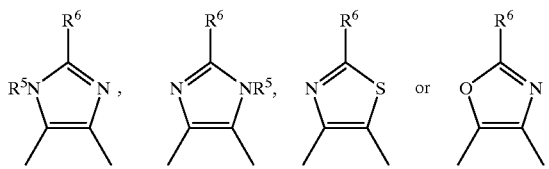

wherein $R^5$ and $R^6$ are the same as those defined above, in particular, imidazole ring.

Examples of the ring C include a benzene ring which may optionally have 1 to 5 substituents selected from the group consisting of:
a) a lower alkyl group, a lower alkenyl group or a lower alkynyl group, each of which is unsubstituted or may substituted with a halogen atom or a hydroxyl group,
b) a lower alkoxy group, a hydroxyl group, a mercapto group or a lower alkylthio group, each of which is unsubstituted or substituted,
c) a halogen atom or a cyano group,
d) a carboxyl group, a lower alkoxycarbonyl group, a lower alkanoyl group, a lower alkanoyloxy group, a carbamoyl group or a lower alkylaminocarbonyl group,
e) an amino group, a mono- or di-lower alkylamino group, a lower alkanoylamino group, a 1-pyrrolidinyl group, a piperidino group, a morpholino group, or a 1-piperazinyl, 1-imidazolidinyl or 1-homopiperazinyl group which may be substituted with a lower alkyl group at the ring nitrogen atom,
f) a cycloalkyl group,
g) a phenyl group which may be substituted, and
h) an imidazolyl, triazolyl, tetrazolyl, pyrrolyl, pyridyl, pyrazinyl or pyrimidinyl group, each of which may be substituted. Preferably, the ring C is a benzene ring which is unsubstituted or substituted with lower alkyl substituted phenyl ring.

Examples of the substituents of the above lower alkyl group, lower alkenyl group and lower alkynyl group include an amino group; a mono- or di-lower alkylamino group; a lower alkanoylamino group substituted with an amino group or a mono- or di-lower alkylamino group; an amino group having a protective group such as an aromatic acyl group, a carbamoyl group, a carbamide group, a phthaloyl group and the like; a 1-pyrrolidinyl group; a piperidino group; a morpholino group; a 1-piperazinyl, 1-imidazolidinyl, 1-homopiperazinyl or 1-pirazinyl group each of which may be substituted with a lower alkyl group at the ring nitrogen atom; a guanidino group; an amidino group; a hydroxyl group; a lower alkoxyl group; a cyano group; a carbamoyl group; a carboxyl group; a lower alkoxycarbonyl group; a lower alkanoyloxy group; and a phenyl, imidazolyl, pyridyl, pyrazinyl, pyrimidinyl, pyridazinyl, pyrazolyl, pyrrolyl, tetrazolyl, triazolyl, thiazolyl or oxazolyl group, each of which may be substituted with a lower alkyl group, a halogen atom, a lower alkoxyl group, an amino group, a mono- or di-lower alkylamino group, a hydroxyl group or a carboxyl group.

Examples of the substituents of lower alkoxy group include a halogen atom, a cyano group, a hydroxyl group, a carboxyl group, a lower alkoxycarbonyl group, a lower alkanoyl group, a lower alkanoyloxy group, a carbamoyl group, a lower alkylaminocarbonyl group and a phthalimido group.

Examples of the substituents of amino group include a lower alkyl group, a lower alkenyl group, a lower alkynyl group and a lower alkanoyl group.

Examples of the substituents of phenyl group include a lower alkyl group, a lower alkenyl group, a lower alkynyl group, a halogen atom, a lower alkoxyl group, an amino group, a mono- or di-lower alkylamino group, a hydroxyl group and a carboxyl group.

Examples of the substituents of imidazolyl, triazolyl, tetrazolyl, pyrrolyl, pyridyl, pyrazinyl and pyrimidinyl group in the above substituents (h) of the ring C include a lower alkyl group, a cycloalkyl group and a phenyl group.

Examples of the halogen atom include fluorine, chlorine, bromine and iodine.

Preferably, A is —NHCO—.

Typical examples of the compound of the formula (I) include
    4'-[(2-methyl-1,4,5,6-tetrahydroimidazo[4,5-d][1]benzazepin-6-yl)carbonyl]-2-phenylbenzanilide,
    4'-[(2-ethyl-1,4,5,6-tetrahydroimidazo[4,5-d][1]benzazepin-6-yl)carbonyl]-2-phenylbenzanilide,
    4'-[(2-cyclopropyl-1,4,5,6-tetrahydroimidazo[4,5-d][1]benzazepin-6-yl)carbonyl]-2-phenylbenzanilide,
    4'-[(2-propyl-1,4,5,6-tetrahydroimidazo[4,5-d][1]benzazepin-6-yl)carbonyl]-2-phenylbenzanilide.

Examples of the pharmaceutically acceptable salts of the compound of the formula (I) include an acid addition salt with a mineral acid such as hydrochloric acid, hydrobromic acid, hydroiodic acid, sulfuric acid, nitric acid, phosphoric acid or the like, an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid or the like, or an acidic amino acid such as aspartic acid, glutamic acid or the like; a salt with an inorganic base such as sodium, potassium, magnesium, calcium, aluminium or the like, an organic base such as methylamine, ethylamine, ethanolamine or the like or a basic amino acid such as lysine, ornithine or the like; and a quaternary ammonium salt.

Examples of other known vasopressin antagonists which can be use in the prevent invention include:
    4-methylamino-1-[4-(3,5-dichlorobenzoylamino)-benzoyl]-1,2,3,4-tetrahydroquinoline,
    1-[4-(N-butylanilinoacetylamino)benzoyl]-2,3,4,5-tetrahydro-1H-benzazepine,
    (1-adamantyl)acetyl-D-(O-ethyl)tyrosyl-phenylalanyl-valyl-asparagyl-ornithyl-prolyl-arginineamide,
    [1-(β-mercapto-β, β-cyclopentamethylenepropionic acid-2-(O-ethyl)-D-tyrosine-4-valine-6-D-cysteine-7-D-arginine-9-desglycine]-vasopressin,
    5-ethoxy-1,3-dihydro-1-[2-methoxy-4-(Δ3-pyrroline-1-yl)benzenesulfonyl]-3-spirocyclohexaneindole-2-one,
    5-ethoxy-1,3-dihydro-1-[2-methoxy-4-(pyrrolidine-1-yl)benzenesulfonyl]-3-spirocyclohexaneindole-2-one, 1-[1-[4-[3-(acetylamino)propoxy]benzoyl]-piperidine-4-yl]-1,2,3,4-tetrahydro-2-quinoline, 5-(dimethylamino)-1-[4-(2-methylbenzamide)-benzoyl]-2,3,4,5-tetrahydro-1H-benzazepine, 1-[[5-chloro-3-(2-chlorophenyl)-1-[(3,4-dimethoxyphenyl)sulfonyl]-2,3-dihydro-3-hydroxy-1H-indole-2-yl]carbonyl-2-pyrrolidinecarboxyamide, 4'-methyl-N-[4-[5-[2-(4-methylpiperazine-1-yl)-2-oxoethyl]-4-oxo-2,3,4,5-tetrahydro-1H-1,5-benzodiazepine-1-ylcarbonyl]phenyl]biphenyl-2-carboxyamide, 2',4'-dimethyl-N-[4-[8-[2-(1-pyrrolidinyl)ethyl]-5,6,7,8-tetrahydro-4H-thieno[2,3-b][1,4]diazepine-4-ylcarbonyl]phenyl]biphenyl-2-carboxyamide, and N-[2,3-dihydro-2-(1-pyrrolidinyl)-1H-indene-1-yl]-N-methyl-3-nitrobenzeneacetoamide, and a pharmaceutically acceptable salt thereof.

The pharmaceutical composition of the present invention can be prepared in a known dosage form of by optionally combining with a pharmaceutically acceptable carrier or excipient according to a known preparation technique such as mixing and dissolving desired components. Although ophthalmic topical administration is useful for prevention and treatment of diseases caused by ocular circulatory disorders in the present invention, systemic administration such as oral administration and injection may also be useful.

For ophthalmic topical administration, the pharmaceutical composition of the present invention can be prepared in the form of aqueous eye drops such as aqueous suspended eye drops, viscous eye drops, gel, aqueous solution, emulsion and the like. It can be also prepared in the form of powder, granules or tablet and is suspended or dissolved in purified water upon use. Further, it can be prepared in the form of non-aqueous eye drops such as oily eye drops and ophthalmic ointment, or lasting or sustained-release eye drops. Eye drops are usually adjusted to pH 3 to 8, preferably pH 4 to 7, and osmotic pressure there of is adjusted to about 230 to 450 mOsm, preferably about 260 to 320 mOsm.

Optionally, additives may be added to the pharmaceutical composition of the present invention. Examples of such additives include preservatives such as parabens (for example, methyl paraoxybenzoate and propyl paraoxybenzoate), invert soaps (for example, benzalkonium chloride, benzethonium chloride, chlorhexidine gluconate and cetylpyridinium chloride), alcohol derivatives (for example, chlorobutanol, phenethyl alcohol and benzyl alcohol), organic acids and their salts (for example, sodium dehydroacetate, sorbic acid and salts thereof), phenols (for example, parachloromethoxyphenol and parachlorometacresol), organomercurials (for example, thimerosal, phenylmercuric acetate and nitromersol) and the like; isotonizing agents such as sodium chloride, sorbitol, mannitol, glycerin and the like; pH adjusting agents such as hydrochloric acid, acetic acid, sodium hydroxide, phosphoric acid and the like; buffers such as phosphates (for example, disodium hydrogenphosphate, sodium dihydrogenphosphate, dipotassium hydrogenphosphate and potassium dihydrogenphosphate), boric acid and salts thereof (for example, borax), citrates, acetates (for example, sodium acetate and ammonium acetate), salts of amino acids (for example, glutamic acid) and the like; stabilizers such as chelating agents (for example, sodium edetate, citric acid and the salt thereof), antioxidants (for example, sulfurous acid and the salt thereof) and the like; thickeners such as polyhydric alcohol (for example, glycerin and macrogol), sugars (for example sorbitol, mannitol and sucrose), celluloses (for example, methylcellulose and sodium carboxymethylcellulose), synthesized high molecular compounds (for example, polyvinyl alcohol, polyvinyl pyrrolidone and carboxyvinylpolymer) and the like; and suspending agents (for example, surfactants in addition to the above thickeners). Examples of the surfactants include nonionic surfactants such as polysorbate and polyoxyethylene hydrogenated castor oil, cationic surfactants such as quaternary ammonium salts, anionic surfactants such as alkylsulfates and amphoteric surfactants such as lecithin. Further, vaseline, lanolin, plastibase and the like can be used as a base of ophthalmic ointment.

In addition to the vasopressin antagonist, the pharmaceutical composition of the present invention may optionally contain or may be used together with one or more other pharmacological active agents. Examples of such pharmacological active agents include parasympathomimetic drugs (for example, pilocarpine and carbachol), cholinesterase inhibitors (for example, physostigmine salicylate, distigmine bromide and echothiopate iodide), sympathomimetic drugs (for example, epinephrine, dipivalyl epinephrine, clonidine, paraamino clonidine and brimonidine), sympathomimetic β-blockers (for example, betaxolol, levobunolol, timolol and carteolol), prostaglandine derivatives (for example, isopropyl unoprostone and latanoprost) for diseases caused by ocular circulatory disorders, and tropicamide for diseases caused by ciliary muscle tension.

The pharmaceutical composition of the present invention is useful for preventing or treating diseases caused by ocular circulatory disorder, for example, glaucoma (in particular, open-angle glaucoma and normal intraocular tension glaucoma), ocular hypertension, retinal pigmentary degeneration, macular degeneration, ischemic optic neuropathy, iridocyclitis, retinal artery occlusion, retinal vein occlusion, diabetic retinopathy, retinochoroidat disorder and asthenopia; and diseases caused by ciliary muscle tension, for example, myopia. In particular it is useful for preventing and treating glaucoma and myopia.

Although the dosage regimen is not specifically limited, in case of an adult man, normally, the desired effect can be obtain by, for example, instillation of a few drops, preferably 1 to 3 drops of eye drops containing 0.001 to 10 w/v%, preferably 0.05 to 5 w/v% of the compound of the formula (I), 2 to 6 times per day.

EXAMPLES

The following Examples and Test Examples further illustrate the present invention in detail but are not to be construed to limit the scope thereof. Compound 1 used in the following Examples and Test Examples is 4'-[(2-methyl-1,4,5,6-tetrahydroimidazo[4,5-d][1]benzazepin-6-yl)carbonyl]-2-phenylbenzanilide monohydrochloride.

Example 1

An aqueous suspended eye drops containing the compound of the present invention was prepared according to the following formulation.

| Component | Amount |
| --- | --- |
| Compound 1 | 1.0 g |
| Sodium dihydrogenphosphate | 0.1 g |
| Polysorbate 80 | 0.1 g |
| Sodium chloride | 0.9 g |
| Sodium hydroxide | q. s. |
| Distilled water | q. s. |
| Total | 100 ml (pH 7.0) |

Example 2

An aqueous suspended eye drops containing the compound of the present invention was prepared according to the following formulation.

| Component | Amount |
| --- | --- |
| Compound 1 | 3.0 g |
| Sodium acetate | 0.1 g |
| Sodium chloride | 0.9 g |
| Sodium carboxymethylcellulose | 0.5 g |
| Methyl paraoxybenzoate | 0.026 g |
| Propyl paraoxybenzoate | 0.014 g |
| Sodium hydroxide | q. s. |
| Distilled water | q. s. |
| Total | 100 ml (pH 6.0) |

Example 3

An aqueous solution containing the compound of the present invention was prepared according to the following formulation.

| Component | Amount |
| --- | --- |
| Compound 1 | 0.1 g |
| Phosphoric acid | 0.1 g |
| Mannitol | 5.0 g |
| Tyloxapol | 0.1 g |
| Benzalkonium chloride | 0.01 g |
| Sodium hydroxide | q. s. |
| Distilled water | q. s. |
| Total | 100 ml (pH 4.5) |

Example 4

An aqueous solution containing the compound of the present invention was prepared according to the following formulation.

| Component | Amount |
| --- | --- |
| 4'-[(2-Ethyl-1,4,5,6-tetrahydroimidazo [4,5-d] [1] benzazepin-6-yl) carbonyl]-2-phenylbenzanilide monohydrochloride | 0.05 g |
| Lactic acid | 0.1 g |
| Glycerin | 2.6 g |
| Polyethylene glycol 4000 | 0.2 g |
| Sodium hydroxide | q. s. |
| Distilled water | q. s. |
| Total | 100 ml (pH 4.0) |

Example 5

A gel preparation containing the compound of the present invention was prepared according to the following formulation.

| Component | Amount |
| --- | --- |
| Compound 1 | 0.5 g |
| Carboxyvinyl polymer | 0.5 g |
| Sodium hydroxide | q. s. |
| Distilled water | q. s. |
| Total | 100 ml (pH 6.5) |

Example 6

An ophthalmic ointment containing the compound of the present invention was prepared according to the following formulation.

| Component | Amount |
| --- | --- |
| 4'-[(2-Cyclopropyl-1,4,5,6-tetrahydroimidazo[4,5-d][1]benzazepin-6-yl)carbonyl]-2-phenylbenzanilide monohydrochloride | 1.0 g |
| Liquid paraffin | 1.0 g |
| White vaseline | ad. 100 g |

Example 7

The compound described hereinafter, lactose, corn starch, ⅔ of crystalline cellulose and ½ of magnesium stearate were mixed and then granulated. To the granules obtained were added the remaining crystalline cellulose and magnesium stearate, and the resultant mixture was compressed to prepare tablets.

The tablets may be coated by sugar according to a conventional method.

| Component | Amount |
| --- | --- |
| 4'-[(2-Propyl-1,4,5,6-tetrahydroimidazo[4,5-d][1]benzazepin-6-yl)carbonyl]-2-phenylbenzanilide monohydrochloride | 10 mg |
| Lactose | 35 mg |
| Corn starch | 150 mg |
| Crystalline cellulose | 30 mg |
| Magnesium stearate | 5 mg |
| One tablet | 230 mg |

Example 8

Compound 1 described hereinafter, lactose, crystalline cellulose and ½ of magnesium stearate were mixed and then granulated. To the granules obtained were added the remaining magnesium stearate and the mixture was filled and sealed into gelatin capsules to prepare a capsule preparation.

| Component | Amount |
| --- | --- |
| Compound 1 | 10 mg |
| Lactose | 90 mg |
| Crystallized cellulose | 70 mg |

-continued

| Component | Amount |
|---|---|
| Magnesium stearate | 10 mg |
| One capsule | 180 mg |

Test Example 1

Ophthalmic Topical Toxicity Test

Test Method

A test drug was instilled in the eye of a pigmented rabbit in an amount of 50 µl, 8 times per day. Immediately after the last instillation, conditions of the cornea, conjunctiva and iris, as well as the presence of any secrete and the eye movement were observed with the naked eye. Further, 30 minutes after the last instillation, the presence of corneal epithelial disorders was observed by instilling fluorescein and using a slit lamp. As the test drug, the suspension of the above Example 1 was used.

Test Results

After instillation of the test drug, conditions of the cornea, conjunctiva and iris as well as the secretion and the eye movement were normal, and no disorder was recognized by observation with the naked eye. Further, no corneal epithelial disorder was recognized by observation using a slit lamp.

From the above results, it was proved that the active component of the present invention, Compound 1, did not has any toxicity for the anterior segment of the eye, and was a safety drug.

Test Example 2

Activity on decrease in blood flow rate in optic disk

Test Method

A test drug was instilled in respective one eyes of 3 pigmented rabbits in an amount of 20 µl and the other eyes were taken as control eyes. Sixty minutes after instillation, 10 µl of 0.002 w/v % desmopressin was injected into the vitreous bodies of both eyes with a microsyringe. The blood flow was measured just prior to instillation of the test drug, at 30 and 60 minutes after instillation as well as at 30, 60 and 90 minutes after injection of desmopressin. The blood flow at the site other than superficial blood vessels of the optic disk was measured by a laser speckle-peripheral circulation analyzer after instillation of tropicamide-phenylephrine eye drops to induce mydriasis. The above suspension of Example 1 was used as the test drug and, for a control group, the base of example 1 (the solution without Compound 1) was instilled.

Test Results

The Results are shown in FIG. 1.

As seen from FIG. 1, in the eyes of the control group, no change in the blood flow was recognized in the optic disk due to instillation of the base. When desmopressin was injected, a decrease in the blood flow rate was recognized. In the eyes of the test drug-instilled group, the blood flow in the optic disk increased at 30 to 60 minutes after instillation. On the other hand, the decrease in the blood flow after injection of desmopressin was clearly smaller than that of the eyes of the control group.

The above results show that the active component of the present invention, Compound 1, improves ocular circulation, topically in the eye.

Test Example 3

Intraocular pressure hypotensive activity by administration into anterior chamber Test Method Three pigmented rabbits having stable intraocular pressure were subjected to topical anesthesia. A 30 G needle was inserted into the anterior chamber through the corneal stroma at about 2 mm from the corneal limbus of one eye and 50 µl of anterior chamber water was collected. Then, the same amount of a test drug was injected through the same site. The other eye was not treated (control eye). Intraocular pressure was measured at 30 minutes prior to injection of the test drug, just prior to injection of the test drug, and 30 minutes and 1, 2, 4, 6 and 24 hour after injection of the test drug with using Pneumatonograph (manufactured by Alcon). The solution of the following formulation was used as the test drug.

Formulation

| Component | Amount |
|---|---|
| Compound 1 | 0.01 g |
| Sodium dihydrogenphosphate (2 hydrate) | 0.1 g |
| Sodium Chloride | 0.9 g |
| Hydrochloric acid | q. s. |
| Distilled water for injection | q. s. |
| Total | 100 ml (pH 4.0) |

The Results are shown in FIG. 2.

As shown in FIG. 2, the intraocular pressure of the control eye which was not treated was stable at 28 to 30 mm Hg in any measurement. On the other hand, the test drug-injected eye showed significant lowering of the intraocular pressure in comparison with the control eye at 30 minutes to 6 hour after injection of the test drug.

The above results show that the active component of the present invention, Compound 1, reduces intraocular pressure by topical administration to the eye.

Test Example 4

Intraocular hypotensive activity by instillation of eye drops

Five pigmented rabbits (about 2 kg body weight) were used. Twenty µl of a test drug was instilled to each rabbit, and a change in intraocular pressure after instillation was measured using Pneumatonograph (manufactured by Alcon) with time. The suspension of Example 1 was used as the test drug.

Test Results

Time for reaching maximal intraocular reduction after instillation of the test drug and the maximal intraocular reduction range are shown in Table 1.

TABLE 1

| Animal Individual No. | Time for reaching maximal intraocular reduction after instillation (hr) | Maximal intraocular reduction range (mmHg) |
|---|---|---|
| No. 1 | 2.0 | 5.8 |
| No. 2 | 2.0 | 3.8 |

TABLE 1-continued

| Animal Individual No. | Time for reaching maximal intraocular reduction after instillation (hr) | Maximal intraocular reduction range (mmHg) |
|---|---|---|
| No. 3 | 2.0 | 4.0 |
| No. 4 | 1.0 | 2.5 |
| No. 5 | 1.0 | 3.0 |

These results show that the active component of the present invention, Compound 1, also exhibits excellent ocular hypotensive activity by administration of eye drops.

Test Example 5

Ciliary Muscle Relaxing Activity

Test Method

White rabbit (about 2 kg weight) was used. Excess amount of pentobarbital sodium was administered to the rabbit intravenously to be euthanized. Immediately after that, the eyeball was removed and stored in Krebs-solution (NaCl: 112 mM, KCl: 5.9 mM, $CaCl_2·2H_2O$: 2.0 mM, $MgCl_2·6H_2O$: 1.2 mM, $NaH_2PO_4·2H_2O$: 1.2 mM, $NaHCO_3$: 25 mM, glucose: 11.5 mM). A specimen of the ciliary muscle was suspended in a Maguns tube filled with Krebs-solution and equilibrated under 20 to 30 mg of resting tension. As a contracting drug, carbachol was used. Five minutes before application of carbachol, a test drug was added to the Maguns tube so that the concentration of Compound 1 was $1×10^{-7}$ M or $1×10^{-8}$ M. A change of contractile response was isometrically recorded on a pen-recorder through a transducer and an amplifier and the effect on a dose-contractile response induced by carbachol was examined. Compound 1 was dissolved in DMSO at a concentration of $10^{-2}$ M and, after dilution with distilled water, it was used as the test drug.

Test Results

Figure 3:
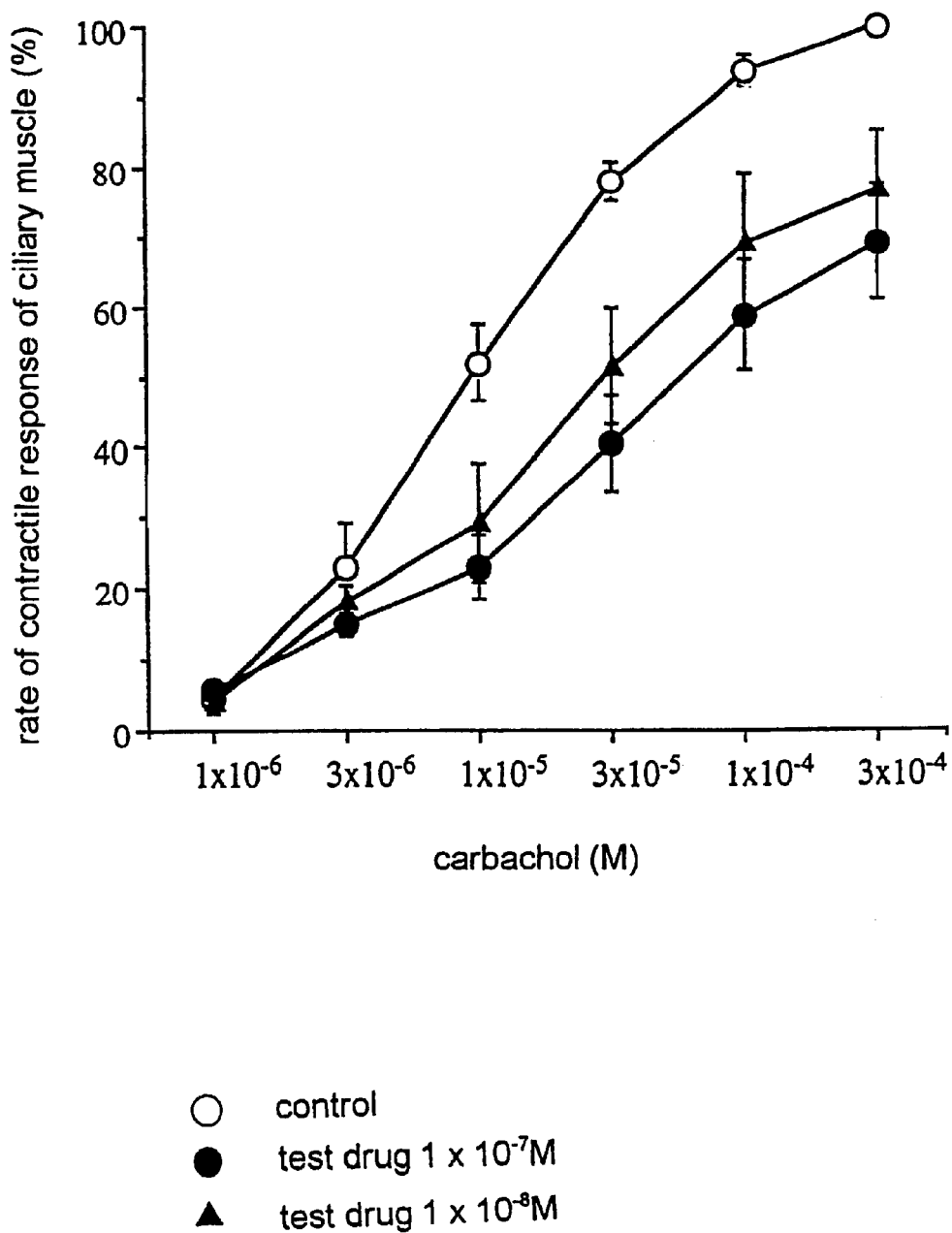
FIG. 3 illustrates the test results of Test Example 5, hereinafter.

The results are shown in FIG. 3. In FIG. 3, the vertical axis represents the rate of contractile response of the ciliary muscle by taking the maximal contractile response of the ciliary muscle upon application of $3×10^{-4}$ M carbachol as 100%. The horizontal axis represents the concentration of carbachol.

As seen from FIG. 3, the ciliary muscle contracted dose-dependently by application of $1×10^{-6}$ to $3×10^{-4}$ M carbachol, and the test drug antagonized against carbachol contraction, non-competitively by addition of $1×10^{-7}$ or $1×10^{-8}$ M test drug.

The above results show that the active component of the present invention, Compound 1, relaxes the ciliary muscle. In addition, as a functional mechanism of the ocular hypotensive activity of Compound 1, it is considered that an increase in uveoscleral outflow of aqueous humor may be related to relaxation of ciliary muscle.

What is claimed is:

1. A method for preventing or treating myopia which comprises administering an effective amount of a vasopressin antagonist to a subject in need thereof.

2. The method according to claim 1, wherein the vasopressin antagonist is a benzazepine derivative represented by the formula (I):

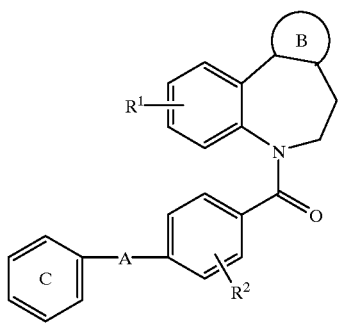

wherein:
ring B is a nitrogen-containing aromatic 5-membered ring having at least one nitrogen atom and optionally one oxygen or sulfur atom which may have substituent(s);
$R^1$ and $R^2$ are the same or different, and each represents a hydrogen atom, a halogen atom, a lower alkyl group, an amino group which may be substituted with lower alkyl group(s), or a lower alkoxy group;
A is a single bond or a group represented by the formula: $—NHCO—(CR^3R^4)_n—$,
n is 0 or an integer of 1 to 3;
$R^3$ and $R^4$ may be the sane or different, and each represents a hydrogen atom or a lower alkyl group, or $R^3$ together with $R^4$ may form a lower alkylene group having 2 to 7 carbon atoms; and
ring C is a benzene ring, which may have substituent(s), or a pharmaceutically acceptable salt thereof.

3. The method according to claim 2, wherein the ring B is represented by the formula:

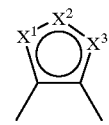

wherein:
one of $X^1$ and $X^3$ is a group represented by the formula: $=N—$, and the other is a group represented by the formula: $—NR^5—$, $—O—$, $—S—$ or $=N—$;
$X^2$ is a group represented by the formula: $=CR^6—$, $—O—$, $—S—$ or $=N—$;
$R^5$ is a hydrogen atom or a lower alkyl group; and
$R^6$ is
a) a hydrogen atom,
b) a lower alkyl group, a lower alkenyl group or a lower alknyl group, each of which is unsubstituted or substituted,
c) a cycloalkyl group having 3 to 8 carbon atoms,
d) an amino group which may have substituent(s), a 1-pyrrolidinyl group, a piperidino group, a morpholino group, or a 1-piperazinyl, 1-imidazolidinyl or 1-homopiperazinyl group which may be substituted with a lower alkyl group at the ring nitrogen atom,
e) a guanidino group or an amidino group, or
f) a hydroxyl group, a lower alkoxyl group, a mercapto group, or a lower alkylthio group; and
the ring C is a benzene ring which may have 1 to 5 substituents selected from the group consisting of:
a) a lower alkyl group, a lower alkenyl group or a lower alkynyl group, each of which is unsubstituted or substituted with a halogen atom or a hydroxyl group, b) a lower alkoxy group, a hydroxyl group, a mercapto group or a lower alkylthio group, each of which is unsubstituted or substituted,
c) a halogen atom or a cyano group,
d) a carboxyl group, a lower alkoxycarbonyl group, a lower alkanoyl group, a lower alkanoyloxy group, a carbamoyl group or a lower alkylaminocarbonyl group,
e) an amino group, a mono- or di-lower alkylamino group, a lower alkanoylamino group, a 1-pyrrolidinyl group, a piperidino group, a morpholino group, or a 1-piperazinyl, 1-imidazolidinyl or 1-homopiperazinyl group which may be substituted with a lower alkyl group at the ring nitrogen atom,
f) a cycloalkyl group,
g) a phenyl group which may be substituted, and
h) an imidazolyl, triazolyl, tetrazolyl, pyrrolyl, pyridyl, pyrazinyl or pyrimidinyl group, each of which may be substituted.

4. The method according to claim 2, wherein the ring B is represented by the formula:

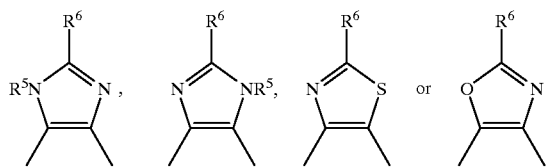

wherein
$R^5$ is a hydrogen atom or a lower alkyl group; and
$R^6$ is
a) a hydrogen atom,
b) a lower alkyl group, a lower alkenyl group or a lower alkynyl group, each of which is unsubstituted or substituted,
c) a cycloalkyl group having 3 to 8 carbon atoms,
d) an amino group which may have substituent(s), a 1-pyrrolidinyl group, a piperidino group, a morpholino group, or a 1-piperazinyl, 1-imidazolidinyl or 1-homopiperazinyl group which may be substituted with a lower alkyl group at the ring nitrogen atom,
e) a guanidino group or an amidino group, or
f) a hydroxyl group, a lower alkoxyl group, a mercapto group, or a lower alkylthio group.

5. The method according to claim 3, wherein the ring C is a benzene ring which is unsubstituted or substituted with a lower alkyl-substituted phenyl group.

6. The method according to claim 3, wherein the A in the formula (I) is —NHCO—.

7. The method according to claim 2, wherein the vasopressin antagonist is 4'-[(2-methyl-1,4,5,6-tetrahydroimidazo[4,5-d][1]benzazepin-6-yl)-carbonyl]-2-phenylbenzanilide or its hydrochloride.

8. The method according to claim 1, wherein the vasopressin antagonist is administered in a form for ocular topical administration.

* * * * *